(12) United States Patent
Weber

(10) Patent No.: US 6,689,912 B2
(45) Date of Patent: Feb. 10, 2004

(54) METHODS FOR PREPARING O-DESMETHYLVENLAFAXINE

(75) Inventor: Beat T. Weber, Zofingen (CH)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/304,871

(22) Filed: Nov. 26, 2002

(65) Prior Publication Data

US 2003/0105358 A1 Jun. 5, 2003

Related U.S. Application Data

(60) Provisional application No. 60/334,953, filed on Dec. 4, 2001.

(51) Int. Cl.$^7$ .............................................. C07C 211/00
(52) U.S. Cl. ....................................... 564/336; 564/409
(58) Field of Search .................................. 564/336, 409

(56) References Cited

U.S. PATENT DOCUMENTS

| 4,535,186 A | 8/1985 | Husbands et al. |
| 4,729,817 A | 3/1988 | Francis et al. |
| 5,043,466 A | 8/1991 | Shepard |

FOREIGN PATENT DOCUMENTS

| WO | WO 00/59851 | 10/2000 |
| WO | WO 00/76955 A1 | 12/2000 |
| WO | WO 02/06453 A2 | 1/2002 |

OTHER PUBLICATIONS

Julia W. Wildes et al., J. Org. Chem., 1971, 721–723, 36(5).

*Primary Examiner*—Samuel Barts
(74) *Attorney, Agent, or Firm*—Rebecca R. Barrett

(57) ABSTRACT

The present invention provides an efficient method of making O-desmethyl-venlafaxine.

15 Claims, No Drawings

METHODS FOR PREPARING O-DESMETHYLVENLAFAXINE

This application claims priority from provisional application serial No. 60/334,953, filed on Dec. 4, 2001, the entire disclosure of which is hereby incorporated by reference.

BACKGROUND OF THE INVENTION

O-desmethylvenlafaxine is a major metabolite of venlafaxine. Methods to make O-desmethylvenlafaxine are described in U.S. Pat. No. 4,535,186. This method uses benzyl blocking groups leading to relatively low throughput.

A process of making O-desmethylvenlafaxine is also described in WO 00/59851 in which venlafaxine is allowed to react with diphenyl phosphide in THF (generated by adding n-butyl lithium in THF to diphenylphosphine in THF below 0° C.) at reflux for an overnight period. The yield was reported to be 73.8%. Furthermore, the method involved extraction steps involving large volumes of solvent.

The present invention provides a process of making O-desmethylvenlafaxine which is both time and material efficient.

DESCRIPTION OF THE INVENTION

In accordance with the present invention is provided a method of making O-desmethylvenlafaxine comprising the steps of demethylating a compound of Formula I to provide a compound of Formula II as described in Scheme I.

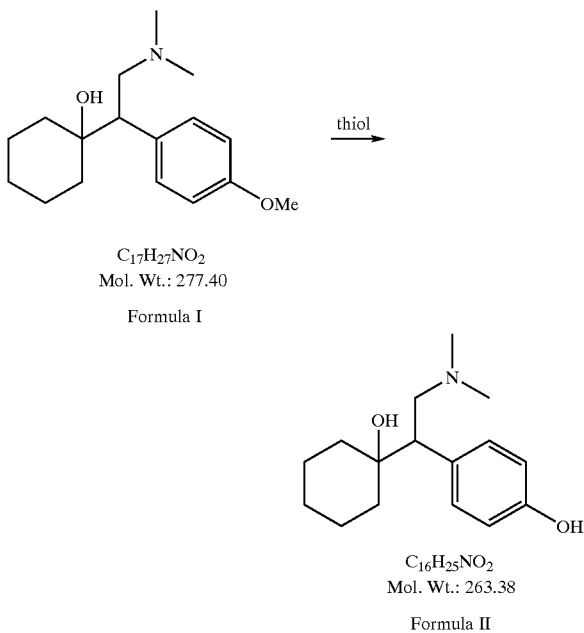

Scheme I $C_{17}H_{27}NO_2$
Mol. Wt.: 277.40

Formula I $C_{16}H_{25}NO_2$
Mol. Wt.: 263.38

Formula II

As described in Scheme I the starting material, venlafaxine (Formula I), is demethylated. Venlafaxine may be prepared in accordance with procedures known in the art such as described in U.S. Pat. No. 4,535,186.

In accordance with the present invention, demethylation is performed using a high molecular weight alkane, arene, or arylalkyl thiolate anion, such as straight or branched chain alkane thiolate anions having 8 to 20 carbon atoms, mono or bicyclic arene thiolate anions having 6 to 10 carbon atoms, or mono or bicyclic arylalkyl thiolate anions having 7 to 12 carbon atoms in the presence of a protic or aprotic solvent. Optionally, a base such as an alkoxide comprised of a straight or branched chain alkyl group of from 1 to 6 carbon atoms may be present to generate the thiolate anion.

Preferably the aliphatic thiol has from 10 to 20 carbon atoms and most preferably the aliphatic thiol is dodecanethiol. The aromatic thiol is preferably benzenethiol. The arylalkyl thiolate anion is preferably toluenethiol or naphthylmethanethiol.

When present, the alkoxide is preferably a lower alkoxide (methoxide, ethoxide and the like) such as sodium methoxide (sodium methylate, sodium methanolate).

The solvent is preferably a hydroxylic or ethereal solvent, and more preferably an alcohol, ethylene glycol or ether of ethylene glycol. Ethers of ethylene glycol include, but are not limited to, ethylene glycol monoethyl ether, triethylene glycol dimethyl ether and polyethylene glycol. Preferably, the solvent is an inert, polar, high boiling point ether of ethylene glycol such as polyethylene glycol and most preferably PEG 400 (polyethylene glycol having a molecular weight range of from about 380–420).

The reaction is performed at a temperature of from about 150° C. to about 220° C., more preferably from about 170° C. to about 220° C., and most preferably from about 180° C. to about 200° C. The reaction is generally allowed to progress until, ideally, not more than 1% venlafaxine remains. In some aspects of the invention the reaction is complete in from about 2 hours to about 5 hours and more preferably in from about 2 to about 3.5 hours.

The thiolate anion can be prepared separately or in situ. In some preferred embodiments of the present invention, venlafaxine base is dissolved in polyethylene glycol 400 containing dodecanethiol and sodium methylate as a solution in methanol as the temperature is increased to from about 180° C. to about 200° C., with stirring for about 2 to about 3.5 hours. In other preferred embodiments of the present invention, venlafaxine base is dissolved in polyethylene glycol containing dodecanethiolate and stirred for about 2 to about 3.5 hours at from about 180° C. to about 200° C. with stirring.

Thereafter the reaction mixture is cooled to between about 65° C. and about 75° C. and an alcohol may be added as a diluent before neutralization to the isoelectric point (about pH9.5 to about pH10.0) with an appropriate neutralization agent such as hydrochloric acid. The alcoholic medium may also aid in the crystallization of the product as neutralization is initiated.

Preferably the alcohol comprises a straight or branched chain alkyl group of 1 to 6 carbon atoms, such as methanol, ethanol, isopropanol, butanol, and the like, and mixtures thereof. In some preferred embodiments of the invention, the alcohol is isopropanol.

Yields of the present invention are greater than about 75% and generally from about 85% to greater than 90%.

The following Examples are illustrative but are not meant to be limiting of the present invention.

EXAMPLE 1

Dodecanethiol (122 g), venlafaxine (111 g), and a methanolic solution of sodium methanolate (30%, 90 g) and PEG 400 are heated to 190° C. The methanol is distilled off and the solution is stirred 2 h at 190° C. Then the temperature is lowered, 2-propanol (450 g) is added and the pH is adjusted to 9.5 with aqueous HCl. The precipitate is collected by suction filtration, and the cake is washed with 2-propanol, toluene, 2-propanol and water. The wet O-desmethylvenlafaxine is dried in vacuo.

Yield: 87 g.

$^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

EXAMPLE 2

Venlafaxine (5.6 g) and benzenethiol sodium salt(6.9 g) are charged to PEG 400 (25 g). The reaction mixture is heated to 160° C. for 5 h. Then the temperature is lowered and water is added (60 g). The pH is adjusted to 3.5 with $H_3PO_4$. The organic by-products are removed by extraction with heptanes (25 g). The pH of the aqueous layer is then adjusted to 9.5 with aqueous ammonia. The precipitate is collected by suction filtration, re-slurried in water (100 g), isolated by suction filtration and dried in vacuo.

Yield 1 g.

$^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

EXAMPLE 3

Dodecanethiol (69 g) venlataxine (55 g) and an ethanolic solution of sodium ethanolate (21%, 82 g) are charged to a pressure vessel. The temperature is raised to 150° C. and the reaction mixture is stirred for 2 days. Then the temperature is lowered and the solution is filtered. The pH of the filtrate is adjusted to 9.5 with aqueous hydrogen chloride. The crystals are collected by suction filtration. The cake is washed with ethanol and dried in vacuo.

Yield: 42 g $^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

EXAMPLE 4

Step a—Formation of the Reagent Sodium Dodecanethiolate

Dodecanethiol (246 g) and sodium methylate in methanol 30% (216 g) are charged to a rotary evaporator. Vacuum is applied and the solvent is abstracted completely using a bath temperature up to 90° C. The remaining sodium dodecanethiolate (272 g) is used without further purification in the subsequent step.

Step b—Demethylation

A mixture of sodium dodecanethiolate (272 g) venlafaxine (256 g) and PEG 400 (185 g) is stirred 3 h at 190° C. Then the temperature is lowered and 2-propanol (915 g) is added and the pH is adjusted to 9.5 with aqueous HCl. The precipitate is collected by suction filtration, and the cake is washed with 2-propanol and water. The wet O-desmethylvenlafaxine is dried in vacuo. Yield: 200 g.

$^1$H-NMR: (Gemini 200, Varian, 200 MHz) (DMSO-d6) δ=9.11 (s, br, 1H; OH), 6.98 (d, br, J=8.4, 2H; arom.), 6.65 (d, br, J=8.4, 2H; arom.), 5.32 (s, br, 1H; OH), 3.00 (dd, J=12.3 and 8.5, 1H), 2.73 (dd, J=8.5 and 6.3, 1H), 2.36 (dd, J=12.3 and 6.3, 1H), 2.15 (s, 6H, 2×Me), 1.7–0.8 (m, 10H, c-hex).

What is claimed:

1. A method of preparing O-desmethylvenlafaxine which comprises reacting venlafaxine with a high molecular weight alkane or arene thiolate anion in an alcohol, ethylene glycol, ether of ethylene glycol, or mixture thereof, to provide O-desmethylvenlafaxine.

2. The method of claim 1 wherein the reaction is performed at about 150° C. to about 220° C.

3. The method of claim 1 wherein the reaction is carried out for about 2 to about 5 hours.

4. The method of claim 1 wherein the thiolate anion is a straight or branched chain alkane thiolate anion having 8 to 20 carbon atoms.

5. The method of claim 1 wherein the thiol is an arene thiolate anion having from 6 to 10 carbon atoms.

6. The method of claim 4 wherein the alkane thiolate anion is dodecanethiolate.

7. The method of claim 5 wherein the arene thiolate anion is benzenethiolate.

8. The method of claim 1 wherein the thiolate anion is generated in the presence of an alkoxide.

9. The method of claim 8 wherein the alkoxide is methoxide.

10. The method of claim 2 wherein the reaction is performed at from about 170° C. to about 220° C.

11. The method of claim 2 wherein the reaction is performed at from about 180° C. to about 200° C.

12. The method of claim 1 further comprising neutralizing the product to the isoelectric point in the presence of an alcohol comprising a straight or branched chain alkyl group of from 1 to 6 carbon atoms.

13. The method of claim 12 wherein the alcohol is isopropanol.

14. The method of claim 12 wherein the isolectric point is about pH9.5 to about pH10.

15. A method of preparing O-desmethylvenlafaxine which comprises the steps of demethylating venlafaxine with dodecyl thiolate and polyethylene glycol 400 in the presence of sodium methylate in methanol at about 180° C. to about 200° C. for about 2 to about 5 hours; and neutralizing the product to about pH 9.5 in the presence of isopropanol.

* * * * *